United States Patent
Grund et al.

(10) Patent No.: US 6,474,993 B1
(45) Date of Patent: Nov. 5, 2002

(54) ARTIFICIAL TISSUE

(75) Inventors: Karl Ernst Grund; Petra C. Köhn; Günter Farin, all of Tübingen (DE)

(73) Assignee: Erbe Elektromedizin GmbH, Tubingen (DE)

(*) Notice: Subject to any disclaimer, the term of this patent is extended or adjusted under 35 U.S.C. 154(b) by 0 days.

(21) Appl. No.: 09/319,317

(22) PCT Filed: Dec. 4, 1996

(86) PCT No.: PCT/EP96/05420

§ 371 (c)(1),
(2), (4) Date: Aug. 9, 1999

(87) PCT Pub. No.: WO98/25254

PCT Pub. Date: Jun. 11, 1998

(51) Int. Cl.$^7$ ................................................ G09B 23/28
(52) U.S. Cl. ..................... 434/262; 623/11.11; 434/295
(58) Field of Search ............................ 623/15.12, 11.11, 623/23.72; 434/262, 295; 602/44, 45, 56

(56) References Cited

U.S. PATENT DOCUMENTS

| | | | | |
|---|---|---|---|---|
| 4,277,367 A | | 7/1981 | Madsen et al. | |
| 4,294,241 A | * | 10/1981 | Miyata | 128/156 |
| 4,455,318 A | * | 6/1984 | Maurice et al. | 426/104 |
| 4,578,354 A | * | 3/1986 | Cannon | 435/178 |
| 5,147,343 A | * | 9/1992 | Kellenberger | 604/368 |
| 5,458,592 A | * | 10/1995 | Abuto et al. | 604/378 |
| 5,531,716 A | * | 7/1996 | Luzio et al. | 604/265 |
| 5,716,726 A | * | 2/1998 | Cheiky | 429/25 |
| 6,006,130 A | * | 12/1999 | Higo et al. | 604/20 |

FOREIGN PATENT DOCUMENTS

DE   195 38 015 A1   3/1997

OTHER PUBLICATIONS

International Preliminary Examination Report, dated Sep. 9, 1998, for PCT/EP96/05420.

* cited by examiner

*Primary Examiner*—Paul B. Prebilic
(74) *Attorney, Agent, or Firm*—St. Onge Steward Johnston & Reens LLC

(57) ABSTRACT

This invention is directed to an artificial tissue comprising a formable composition comprising a hydrogel, an electrolyte, and combustible fibers, said composition being useful for modeling organs, parts of organs, or systems of organs. The artificial tissue exhibits properties allowing training of special surgical techniques, particularly those making use of surgical high-frequency effects.

19 Claims, No Drawings

ARTIFICIAL TISSUE

FIELD OF THE INVENTION

This invention is directed to an artificial tissue as well as artificial organs, parts of organs, or systems of organs and also the use of artificial tissues or artificial organs for surgery training.

BACKGROUND OF THE INVENTION

Artificial organs, parts of organs, or systems of organs for teaching purposes in the field of anatomy have been known for many decades. However, there are no artificial organs, parts of organs, or systems of organs which can be used for training in respect of special diagnostic and/or interventional procedures such as, for example, surgical high-frequency procedures or the like.

However, training with artificial organs, parts of organs, or systems of organs is extremely important particularly in the field of rigid and flexible endoscopy in order to allow one to learn how to safely manipulate the endoscopic instruments.

It is well known that endoscopic surgical procedures such as, for example, endoscopic polypectomy and the transurethral resection of the prostate comprise a relatively large number of variable and interdependent parameters so that comprehensive training is most important to the safe use and to avoiding complications in case of such surgical procedures.

An important parameter with all surgical procedures making use of high-frequency surgery resides in the high-frequency power the intensity of which is decisive both for coagulation and for operating. Adjusting the respective power and guiding the surgical instrument require experience and skill which can only be acquired by corresponding training.

Coagulation means the application of electrical high-frequency a.c. current for endogenic local heating of biological tissue, heating being employed up to a temperature at which intracellular and extracellular colloidal constituents of tissue undergo sol-gel-transformation. Any additional heating of the coagulated tissue will result in drying up, i.e. desiccation, whereby the volume of the tissue shrinks. Further heating of the desiccated tissue leads to carbonization, i.e. combustion. The aforementioned three thermally induced stages of necrosis differ from each other merely by the amount of heat required for each stage.

This already shows that substantial experience is required for a person to be able to successfully employ the desired technique. As an example, in some cases coagulation will suffice for efficient hemostasis while in others desiccation will suffice. Cutting by means of surgical high-frequency procedures requires the supply of energy in such a way that endogenic heating of the biological tissue is effected selectively and quickly up to a temperature at which intracellular and extracellular water is vaporized at such speed that the cell membranes will burst due to the sudden vapor pressure.

Additional difficulties will arise when, in the field of gastroenterology, coagulation procedures are to be performed by means of argon plasma with the aid of endoscopic instruments.

It is therefore the object of this invention to provide an artificial tissue as well as artificial organs which effectively permit realistic training directed to the handling of surgical procedures.

SUMMARY OF THE INVENTION

It is the basic concept of this invention to provide an artificial tissue which, on the one hand, exhibits suitable electrical conductivity so that the physical effects will occur which allow cutting during high-frequency surgery while water to be vaporized is still bound within the tissue, and on the other hand means are provided which are equal to solid organic tissue constituents so that combustion thereof will be possible analogous to natural tissue.

Moreover, in accordance with the basic concept of this invention the artificial tissue is capable of being shaped so that natural organs, parts of organs, or systems of organs may be modeled.

In accordance with this invention the use of shape-retaining hydrogels is proposed for the artificial tissue. Additionally, an electrolyte as well as combustible fibers, for example cotton or the like, are added to the mixture for forming the tissue.

Natural tissues having different structures or structural distributions may be modeled due to the fact that, in accordance with a further basic concept of this invention, different mixing ratios of the above listed ingredients may be realized, and different artificial tissues based on different mixing ratios may be combined within a tissue structure.

In one embodiment colorants are added to the artificial tissue so that an appearance may be obtained which corresponds to the natural tissue. Advantageously, colorants are employed which exhibit one or more color changes at one or more different defined temperatures, for example at the temperature at which natural human tissue will coagulate thermally. Advantageously, thermocolors are employed which undergo a change of color within the temperature range of from 50 to 100° C. It is thereby possible to observe and control the temperature development in the artificial tissue during and after a cutting and/or coagulation procedure.

When artificial tissues are employed which exhibit one or more temperature-dependent changes of color, these may be used in the training of cutting effects, on the one hand, but also in the training of thermal coagulation procedures such as, for example, monopolar or bipolar contact coagulation, argon-plasma coagulation and laser coagulation.

In accordance with a further basic concept of this invention a hygroscopic agent such as glycerol is added to the mixture for forming artificial tissues so that undesirable premature desiccation is inhibited. Moreover, the admixture of glycerol improves combustion of the fibers contained in the tissue. Likewise, the admixture of preserving agents known from food chemistry to suppress mold growth is advantageous.

In accordance with this invention it is possible to shape organs, parts of organs, or systems of organs from the artificial tissues, which may be used not only to represent the anatomy and pathological changes but also for training purposes in the field of surgical interventions.

This enables the surgeon to recognize the respective pathological changes such as polyps, tumors, ulcers etc., on the one hand, and also to surgically treat or remove such pathologic changes in training, for example by cutting, coagulating, vaporizing, argon-plasma coagulating, and laser application.

A specific embodiment of this invention is based on the feature that vascular structures and body cavities may be formed in the artificial tissues to be filled with X-ray contrast media, concrements, liquids or gases so as to permit training of diagnostic procedures such as imaging procedures as well as combined procedures such as papillotomy or stone extraction. Artificial body cavities of this type are also used for training purposes concerning endoscopic surgery procedures making use of high frequency.

To summarize, this invention has succeeded in providing an artificial tissue which particularly in the case of cutting or coagulation by means of high-frequency current and laser application shows effects that are very similar to those occurring in natural human tissue.

Due to the electrical conductivity it is possible for high-frequency current to flow whereby endogenic heat is generated. This in turn leads to the formation of vapor resulting in desiccation. Since the hydrogels employed undergo gel-sol transformation, i.e. melt at elevated temperatures and the admixed combustible fibers can be cut only at a sufficient high-frequency voltage so that an electric arc will be formed between the cutting electrode and the tissue, effects may be obtained which are similar to the behavior of solid organic tissue components.

Below, this invention will be explained in detail with reference to an embodiment thereof.

DETAILED DESCRIPTION OF THE INVENTION

An artificial tissue from which natural organs, parts of organs, or systems of organs were formed comprises a hydrous material, particularly a hydrogel, to which an electrolyte such as sodium chloride, potassium chloride, calcium chloride or the like has been admixed. Moreover, the composition from which the artificial tissue is made contains combustible fibers such as cotton, linen, or comber waste obtained in the production of sheep's wool.

For example, a mixture comprising 4% of agar and 96% of water (93.5% of water and 2.5% of glycerol) or 20.8% of gelatin and 75.2% of water is employed as a shape-retaining hydrogel.

Similarly, other gels may be employed, i.e. particulate systems rich in liquids and gases and composed of at least two components, said systems comprising a colloidally dispersed substance and water as the dispersant. Advantageously, the above-mentioned agar is used which is a commercially available, gel-forming heteropolysaccharide. Even in a 1% solution agar will form a solid gel having a melting point of from 80 to 100° C. so that it may be used to advantage. The employed hydrogels combine hydrophilic properties with water-insoluble properties and ensure the desired shape retention. The electrolyte added to the composition functions to retain the desired electrical conductivity, and the existing fibers cause some mechanical resistance upon cutting of the tissue; said resistance corresponds to the natural resistance and can only be overcome when the energy such as the high-frequency voltage is sufficiently high to cause an arc to be generated between the cutting electrode and the tissue whereby the fiber inside the arc will be burnt.

The electrical conductivity due to the electrolyte enables high-frequency current to flow inside the artificial tissue so that endogenic heat will be generated. Such heat leads to the formation of vapor and to desiccation of the artificial tissue. As mentioned above, combustible fibers are added to the artificial tissue in order to obtain a cutting effect which corresponds to that of high-frequency surgery in natural human tissue where solid organic tissue components will inhibit the unpowered passage of the cutting electrode therethrough due to melting of the tissue. In other words, the admixture of combustible fibers such as cotton or the like to the hydrogel will result in a simulation of the properties of natural human tissue so that the artificial tissue in accordance with the mentioned composition will exhibit similar properties as regards the effect of cutting with high-frequency current.

In a further embodiment a colorant is added to the artificial tissue having the mentioned composition so that a suitable natural appearance may result. It is particularly advantageous to employ colorants in which changes of color occur within predetermined temperature ranges. It is advantageous to employ thermocolors, as they are called, which exhibit a change of color within the temperature range of from 50 to 100° C. When such colorants are employed it is possible to observe and control the temperature development within the artificial tissue during and after a cutting and/or coagulation procedure so that training and learning effects will improve.

In a case where artificial tissues are employed that exhibit one or several temperature-dependent changes of color these tissues are suitable not only for training in respect of cutting effects but also for training in respect of thermal coagulation procedures such as, for example, monopolar or bipolar contact coagulation, argon-plasma coagulation or laser coagulation.

In a further embodiment a differential artificial tissue structure is modeled by individual tissue components having different mixing ratios as regards the hydrogel and the amount of fibers and electrolytes, so that different physical properties may be simulated. Additionally, different colors may be admixed to the differently composed artificial tissues so that the tissue structures will become visually distinct.

It has been found that the admixture of hygroscopic agents such as glycerol or the like prevents premature drying-out of the artificial tissue whereby the storage life and usability thereof is ensured for prolonged periods. Also, the admixture of glycerol will improve combustion of the fibers during the cutting procedure. The preserving agent to be added may for instance be 0.1% sorbic acid (trans-trans-2,4-hexadienoic acid) or a mixture of 0.3% PHB ester (0.21% of p-hydroxybenzoic acid methyl ester and 0.09% of p-hydroxybenzoic acid propyl ester).

On account of the fact that the composition can be shaped it is possible in accordance with another embodiment to model artificial organs, parts of organs, or systems of organs exhibiting anatomical and/or pathologic abnormalities or findings, respectively, so that suitable surgical interventions and in particular endoscopic procedures may be performed in training. In particular for training endoscopic operation techniques, the artificial organs, parts of organs, or systems of organs may include body cavities formed therein so that diagnostic procedures, on the one hand, and surgical operation techniques, on the other hand, may be tested and acquired, as explained above. However, pathologic tissue structures such as, for example, polyps and/or tumors can be shaped with the artificial tissue according to this invention to be inserted into organs, parts of organs, or systems of organs that are likewise artificial.

The artificial tissues, organs, parts of organs, or systems of organs in accordance with the above embodiments ensure the effects required particularly for high-frequency surgery, viz. sufficient electrical conductivity, vaporizing of included water during high-frequency treatment, and combustion of solid organic ingredients when an arc, for example an electric arc, is generated between the cutting electrode and the tissue. Moreover, the tissue in accordance with this invention may also be employed for practicing other thermal operating procedures using, for example, laser, cauterization or microwaves; in these cases, however, the admixture of electrolytes to simulate electrical conductivity is not required.

It is within the concept of this invention that the artificial tissue may comprise bone-like supporting structures so that the possibilities of practicing and training operation procedures are further improved.

What is claimed is:

1. An artificial tissue for surgery training, characterized by a formable composition comprising a hydrogel, an electrolyte, and combustible fibers, characterized in that said hydrogel contains agar and water and further characterized by the admixture of colorants so as to simulate the colors of natural tissue.

2. An artificial tissue for surgery training, characterized by a formable composition comprising a hydrogel, an electrolyte, and combustible fibers, characterized in that said hydrogel contains gelatin and water and further characterized by the admixture of glycerol for purposes of preservation.

3. The tissue as claimed in claim 1, characterized in that said hydrogel is a hydrophilic, water-insoluble polymer.

4. The tissue as claimed in claim 1, characterized in that said electrolyte is sodium chloride, potassium chloride or calcium chloride.

5. The tissue as claimed in claim 1, characterized in that said combustible fibers comprise cotton, linen or comber waste.

6. The tissue as claimed in claim 1, characterized in that said colorants exhibit one or several changes of color within temperature range of from 50 to 100° C.

7. The tissue as claimed in claim 1, characterized by the admixture of a hygroscopic agent for purposes of preservation.

8. An artificial organ for surgery training formed at least in part of tissue characterized by a formable composition comprising a hydrogel, an electrolyte, and combustible fibers, characterized in that said hydrogel contains agar and water and further characterized in that said organ is formed at least in part by a plurality of tissues of different mixing ratios.

9. The organ as claimed in claim 8, characterized in that said electrolyte is sodium chloride, potassium chloride or calcium chloride.

10. The organ as claimed in claim 8, characterized in that said combustible fibers comprise cotton, linen or comber waste.

11. The tissue as claimed in claim 7, characterized by the hygroscopic agent comprising glycerol.

12. The tissue as claimed in claim 2, characterized in that said hydrogel is a hydrophilic, water-insoluble polymer.

13. The tissue as claimed in claim 2, characterized in that said electrolyte is sodium chloride, potassium chloride or calcium chloride.

14. The tissue as claimed in claim 2, characterized in that said combustible fibers comprise cotton, linen or comber waste.

15. The tissue as claimed in claim 2, characterized by the admixture of colorants so as to simulate the colors of natural tissue.

16. The tissue as claimed in claim 15, characterized in that said colorants exhibit one or several changes of color within a temperature range of from 50 to 100° C.

17. An artificial organ for surgery training formed at least in part of tissue characterized by a formable composition comprising a hydrogel, an electrolyte, and combustible fibers, characterized in that said hydrogel contains gelatin and water and further characterized in that said organ is formed at least in part by a plurality of tissues of different mixing ratios.

18. The organ as claimed in claim 17, characterized in that said electrolyte is sodium chloride, potassium chloride or calcium chloride.

19. The organ as claimed in claim 17, characterized in that said combustible fibers comprise cotton, linen or comber waste.

* * * * *